(12) United States Patent
Sugitani

(10) Patent No.: US 8,748,664 B2
(45) Date of Patent: Jun. 10, 2014

(54) DIAMINE COMPOUND AND PRODUCTION METHOD THEREOF

(75) Inventor: Tooru Sugitani, Osaka (JP)

(73) Assignee: Nitto Denko Corporation, Osaka (JP)

( * ) Notice: Subject to any disclaimer, the term of this patent is extended or adjusted under 35 U.S.C. 154(b) by 0 days.

(21) Appl. No.: 13/579,168

(22) PCT Filed: Feb. 24, 2011

(86) PCT No.: PCT/JP2011/001066
§ 371 (c)(1),
(2), (4) Date: Aug. 15, 2012

(87) PCT Pub. No.: WO2011/105088
PCT Pub. Date: Sep. 1, 2011

(65) Prior Publication Data
US 2013/0006017 A1    Jan. 3, 2013

(30) Foreign Application Priority Data

Feb. 24, 2010  (JP) .................................. 2010-038661

(51) Int. Cl.
*C07C 213/00* (2006.01)
(52) U.S. Cl.
USPC ........................................................ 564/418
(58) Field of Classification Search
None
See application file for complete search history.

(56) References Cited

U.S. PATENT DOCUMENTS

| | | | |
|---|---|---|---|
| 3,592,819 A | 7/1971 | Fleming et al. | |
| 2005/0171079 A1 | 8/2005 | Schrimpf et al. | |
| 2005/0234031 A1 | 10/2005 | Schrimpf et al. | |

FOREIGN PATENT DOCUMENTS

| JP | 2004-506795 | 3/2004 |
|---|---|---|
| JP | 2005-187661 | 7/2005 |

*Primary Examiner* — Clinton Brooks
(74) *Attorney, Agent, or Firm* — Hamre, Schumann, Mueller & Larson, P.C.

(57) ABSTRACT

The present invention provides a novel diamine compound represented by formula (1) below. A in formula (1) denotes an optionally-substituted divalent aliphatic group (having a carbon number of 10 or less) or an optionally-substituted divalent aromatic group (having the number of rings of 4 or less), for example. The diamine compound of the present invention can be used as a raw material or a crosslinking agent for polyamide, polyimide, polyurethane, epoxy resin, etc.

(1)

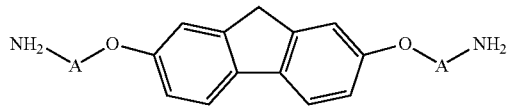

3 Claims, 1 Drawing Sheet

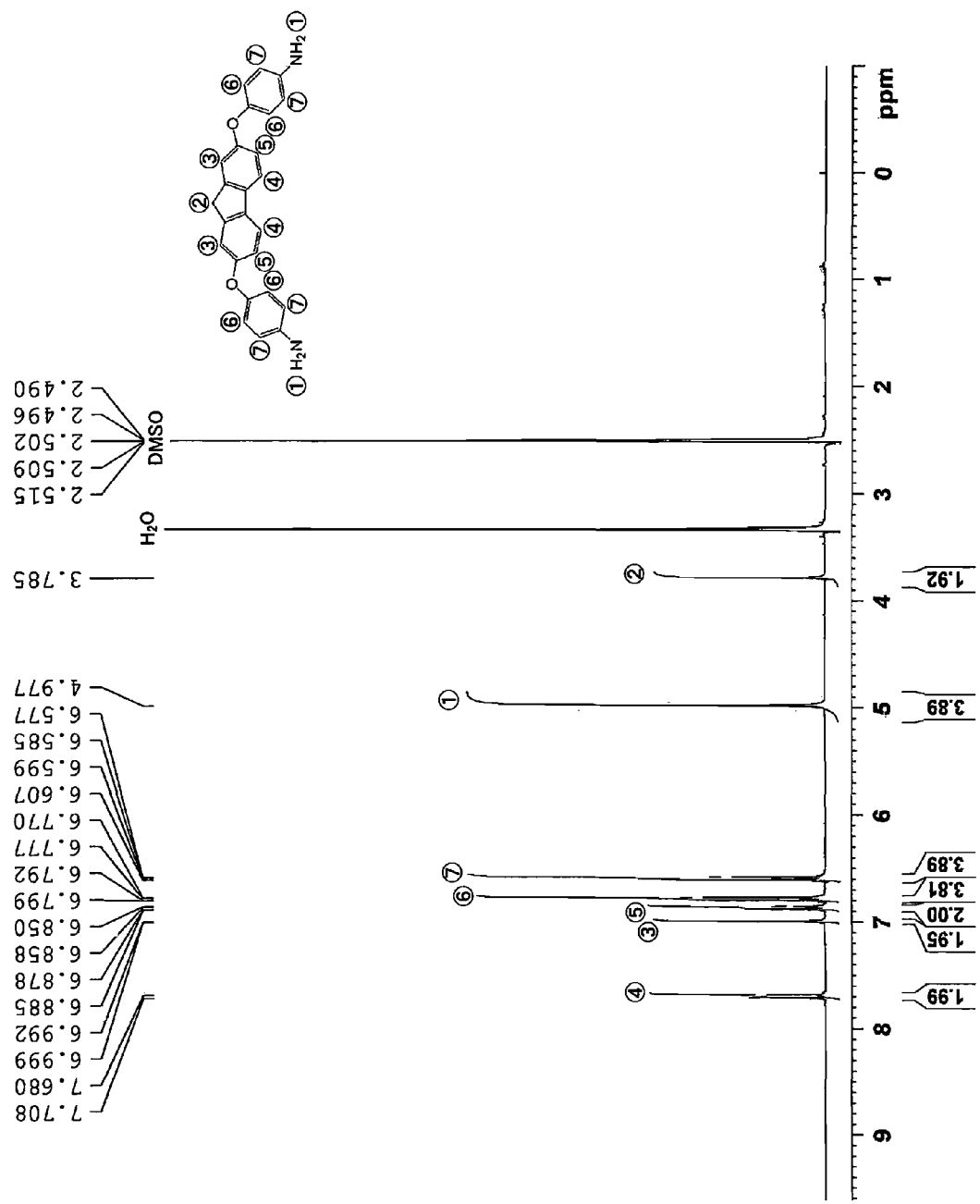

DIAMINE COMPOUND AND PRODUCTION METHOD THEREOF

TECHNICAL FIELD

The present invention relates to a novel diamine compound having a fluorene skeleton, and a method for producing the compound.

BACKGROUND ART

Diamine compounds are widely used as a raw material or a crosslinking agent for thermosetting polymers or polycondensation polymers such as polyamide, polyimide, epoxy resin, and polyurethane. Fluorene has a fused ring structure composed of three rings and has a high planarity of the molecular structure. By allowing such a diamine compound to have a fluorene skeleton, properties derived from the high planarity of the fluorene skeleton are expected to be given to polymers formed using this compound as a raw material or a crosslinking agent.

The carbon atom located at the 9-position in the fluorene skeleton is the carbon atom of a methylene group, which has a higher reactivity compared to the other carbon atoms in the skeleton. Therefore, conventionally, a number of diamine compounds (see Patent Literatures 1 and 2) that have a fluorene skeleton in which substituent having amino group is bonded to the carbon atom at the 9-position in the skeleton, such as 9,9-bis(4-aminophenyl)fluorene, 9,9-bis(4-amino-3-methylphenyl)fluorene, 9,9-bis(4-amino-3-fluorophenyl)fluorene, and 9,9-bis[4-(4-aminophenoxy)phenyl]fluorene, are synthesized and commercially available. Hereinafter, the 9-position, the 2-position, and the 7-position in the fluorene skeleton may be abbreviated simply as "the 9-position", "the 2-position", and "the 7-position", respectively, by omitting the phrase "in the fluorene skeleton".

CITATION LIST

Patent Literature

Patent Literature 1: JP 2005-187661 A
Patent Literature 2: JP 2004-506795 A

SUMMARY OF INVENTION

Technical Problem

However, it is difficult for a diamine compound that has a fluorene skeleton in which a substituent having an amino group is bonded to the carbon atom at the 9-position to exhibit properties derived from the high planarity of the skeleton because the fluorene skeleton is oriented perpendicular to the polymer main chain of this compound, for example, when forming a polycondensation polymer using such a compound. In order to obtain a polymer taking advantage of the planarity of the fluorene skeleton, a substituent having an amino group is at least required to be bonded to each of the carbon atoms at the 2-position and the 7-position, not to the 9-position, in the skeleton. Further, a diamine compound in which no substituent is bonded to the carbon atom at the 9-position is desired so as not to impair the original planarity of the fluorene skeleton.

It is impossible to synthesize such a diamine compound using conventional methods since the carbon atom at the 9-position in the fluorene skeleton has high reactivity. Even if the synthesis were possible, a number of by-products in which a substituent is bonded to the carbon atom at the 9-position are generated. Therefore, the yield rate of the desired diamine compound is significantly reduced, in addition that great efforts are required for purification of the diamine compound.

It is an object of the present invention to provide a novel diamine compound having a fluorene skeleton in which a substituent having an amino group is bonded to each of the carbon atoms at the 2-position and the 7-position, with no substituent being bonded to the carbon atom at the 9-position, and to provide a production method that allows efficient synthesis of the compound.

Solution to Problem

The diamine compound of the present invention is a compound represented by formula (1) below.

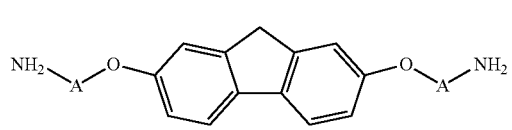

A in formula (1) denotes: a divalent aliphatic group $R^1$ which may have a substituent and has a carbon number of 1 to 10; a divalent aromatic group $Ar^1$ which has 1 to 4 ring structures and may have a substituent; a group, composed of divalent aromatic groups $Ar^2$ and $Ar^3$ each of which has 1 to 4 ring structures and may have a substituent, represented by the formula [—$Ar^2$—$Ar^3$—] (where $Ar^2$ and $Ar^3$ may be the same as or different from each other); a group, composed of divalent aromatic groups $Ar^4$ and $Ar^5$ each of which has 1 to 4 ring structures and may have a substituent, and Z which is an ether group (—O—), a thioether group (—S—) or a sulfone group (—$SO_2$—), represented by the formula [—$Ar^4$—Z—$Ar^5$—] (where $Ar^4$ and $Ar^5$ may be the same as or different from each other); a group, composed of a divalent aromatic group $Ar^6$ which has 1 to 4 ring structures and may have a substituent, and a divalent aliphatic group $R^2$ which may have a substituent and has a carbon number of 1 to 10, represented by the formula [—$Ar^6$—$R^2$—]; or a group, composed of divalent aromatic groups $Ar^7$ and $Ar^8$ each of which has 1 to 4 ring structures and may have a substituent, and a divalent aliphatic group $R^3$ which may have a substituent and has a carbon number of 1 to 10, represented by the formula [—$Ar^7$—$R^3$—$Ar^8$—] (where $Ar^7$ and $Ar^8$ may be the same as or different from each other). The substituent which the aliphatic groups $R^1$, $R^2$, and $R^3$, and the aromatic groups $Ar^1$ to $Ar^8$ may have is at least one selected from a methyl group, an ethyl group, a propyl group, a butyl group, a trifluoromethyl group, a phenyl group, a phenoxy group, a phenylthio group, and a benzenesulfonyl group.

As a result of studies on the synthesis method for such a diamine compound, the inventors have found that the formation of by-products in which a substituent is bonded to the carbon atom at the 9-position is suppressed and efficient synthesis of the diamine compound of the present invention is achieved by: (1) using 2,7-dihydroxy-9-fluorenone in which the carbon atom at the 9-position in the fluorene skeleton forms a ketone group (>C═O) (that is, the 9-position in the fluorene skeleton is a ketone group) and a hydroxy group is bonded to each of the carbon atoms at the 2-position and the 7-position, as a starting material, (2) introducing a substituent having a nitro group to each of the 2-position and the 7-position through a condensation reaction with the hydroxy group, while preventing binding of a substituent to the carbon atom at the 9-position by protecting this carbon atom with the ketone group, (3) reducing the carbon atom at the 9-position to the state where a hydroxy group is bonded thereto and thereafter once acetylating the hydroxy group to form an acetoxy group (—OAc), and (4) reducing, to amino groups, the nitro groups included in the substituents that are bonded to the carbon atoms at the 2-position and the 7-position, as well as reducing, to a methylene group (—CH$_2$—), the carbon atom at the 9-position to which the acetoxy group is bonded.

That is, the method for producing a diamine compound of the present invention is a method for producing the above-mentioned diamine compound of the present invention and includes the steps of obtaining a compound (B) represented by formula (4) by a condensation reaction between 2,7-dihydroxy-9-fluorenone represented by formula (2) and a compound (A) represented by formula (3),

(2)

(3)

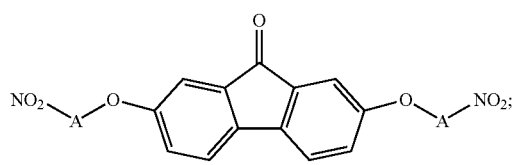

(4)

obtaining a compound (C) represented by formula (5) by reducing the ketone group at the 9-position in the fluorene skeleton of the compound (B) to the state where a hydroxy group is bonded to the carbon atom at the 9-position and thereafter acetylating the hydroxy group,

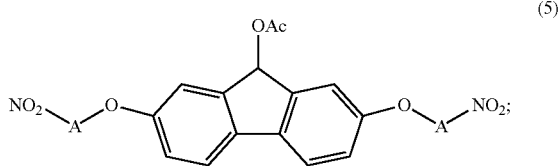

(5)

and obtaining a diamine compound represented by formula (1) by reducing the carbon atom at the 9-position, to which the acetoxy group is bonded, in the fluorene skeleton of the compound (C) and the nitro groups included in the compound (A)-derived substituents that are bonded to the carbon atoms at the 2-position and the 7-position in the skeleton,

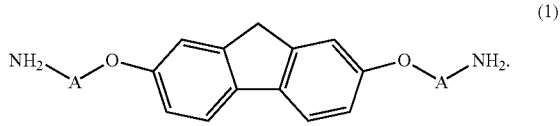

(1)

X in formula (3) denotes halogen group. A in formulae (1) and (3) to (5) denotes: a divalent aliphatic group $R^1$ which may have a substituent and has a carbon number of 1 to 10; a divalent aromatic group $Ar^1$ which has 1 to 4 ring structures and may have a substituent; a group, composed of divalent aromatic groups $Ar^2$ and $Ar^3$ each of which has 1 to 4 ring structures and may have a substituent, represented by the formula [—$Ar^2$—$Ar^3$—] (where $Ar^2$ and $Ar^3$ may be the same as or different from each other); a group, composed of divalent aromatic groups $Ar^4$ and $Ar^5$ each of which has 1 to 4 ring structures and may have a substituent, and Z which is an ether group (—O—), a thioether group (—S—) or a sulfone group (—SO$_2$—), represented by the formula [—$Ar^4$—Z—$Ar^5$—] (where $Ar^4$ and $Ar^5$ may be the same as or different from each other); a group, composed of a divalent aromatic group $Ar^6$ which has 1 to 4 ring structures and may have a substituent, and a divalent aliphatic group $R^2$ which may have a substituent and has a carbon number of 1 to 10, represented by the formula [—$Ar^6$—$R^2$—]; or a group, composed of divalent aromatic groups $Ar^7$ and $Ar^8$ each of which has 1 to 4 ring structures and may have a substituent, and a divalent aliphatic group $R^3$ which may have a substituent and has a carbon number of 1 to 10, represented by the formula [—$Ar^7$—$R^3$—$Ar^8$—] (where $Ar^7$ and $Ar^8$ may be the same as or different from each other). The substituent which the aliphatic groups $R^1$, $R^2$, and $R^3$, and the aromatic groups $Ar^1$ to $Ar^8$ may have is at least one selected from methyl group, ethyl group, propyl group, butyl group, trifluoromethyl group, phenyl group, phenoxy group, phenylthio group, and benzenesulfonyl group.

Advantageous Effects of Invention

The diamine compound of the present invention has a fluorene skeleton in which a substituent having an amino group is bonded to each of the carbon atoms at the 2-position and the 7-position. In addition to this, no substituent is bonded to the carbon atom at the 9-position in the skeleton. Thermosetting polymers or polycondensation polymers provided with properties derived from the high planarity of the fluorene skeleton, for example, are expected to be formed by using such a diamine compound.

In the method for producing a diamine compound of the present invention, the diamine compound of the present invention can be produced efficiently by using 2,7-dihydroxy-9-fluorenone as a starting material, introducing a nitro group-containing substituent to each of the carbon atoms at the 2-position and the 7-position through a condensation reaction of a hydroxy group and simultaneously protecting the carbon atom at the 9-position with a ketone group, reducing the ketone group at the 9-position to a methylene group after the state where a hydroxy group is first bonded to the carbon atom and then an acetoxy group is bonded thereto, and reducing the nitro group in the nitro group-containing substituent to an amino group, thereby introducing a substituent having an amino group to each of the carbon atoms at the 2-position and the 7-position in the fluorene skeleton, while preventing binding of a substituent to the carbon atom at the 9-position.

BRIEF DESCRIPTION OF DRAWING

FIG. 1 is a graph showing a result of the proton nuclear magnetic resonance spectroscopy ($^1$H-NMR) that identifies 2,7-bis(4-aminophenoxy)fluorene synthesized in the example.

DESCRIPTION OF EMBODIMENTS

<Diamine Compound of the Present Invention>

The diamine compound of the present invention is a compound represented by formula (1) below. A in formula (1) is as mentioned above. In the case of $Ar^1$ to $Ar^8$ having a plurality (2 to 4) of ring structures, $Ar^1$ to $Ar^8$ have a fused-ring structure composed of the plurality of rings.

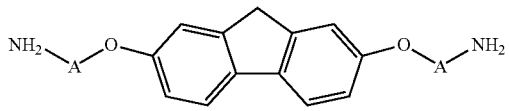

(1)

A in formula (1) is a divalent hydrocarbon group which may have a substituent and has a carbon number of 1 to 10, for example. As a preferred example, formula (1) is a compound represented by formula (6), (7), (8), (9), (10), or (11) below.

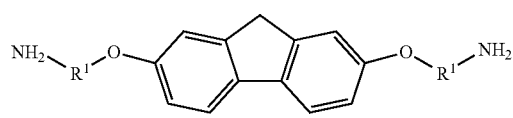

(6)

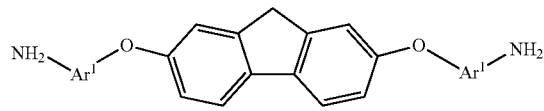

(7)

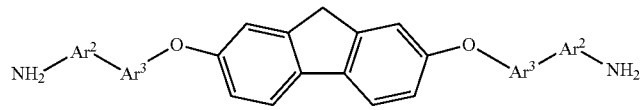

(8)

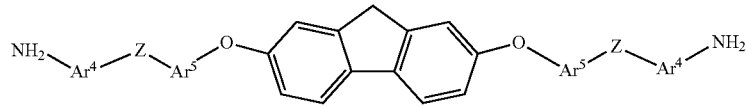

(9)

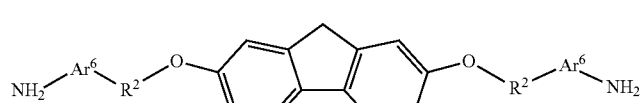

(10)

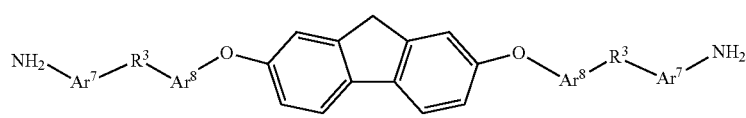

(11)

$R^1$ in formula (6) denotes a divalent aliphatic group which may have a substituent and has a carbon number of 1 to 10. $Ar^1$ in formula (7) denotes a divalent aromatic group which has 1 to 4 ring structures and may have a substituent. $Ar^2$ and $Ar^3$ in formula (8) each independently denote a divalent aromatic group which has 1 to 4 ring structures and may have a substituent. In formula (9), $Ar^4$ and $Ar^5$ each independently denote a divalent aromatic group which has 1 to 4 ring structures and may have a substituent, and Z denotes an ether group (—O—), a thioether group (—S—), or a sulfone group (—SO$_2$—). In formula (10), $Ar^6$ denotes a divalent aromatic group which has 1 to 4 ring structures and may have a substituent, and $R^2$ denotes a divalent aliphatic group which may have a substituent and has a carbon number of 1 to 10. In formula (11), $Ar^7$ and $Ar^8$ each independently denote a divalent aromatic group which has 1 to 4 ring structures and may have a substituent, and $R^3$ denotes a divalent aliphatic group which may have a substituent and has a carbon number of 1 to 10. In the case of $Ar^1$ to $Ar^8$ having a plurality (2 to 4) of ring structures, $Ar^1$ to $Ar^8$ have a fused-ring structure composed of the plurality of rings.

The aliphatic groups $R^1$, $R^2$, and $R^3$ in formulae (1), (6), (10), and (11) each are preferably a saturated aliphatic group. The aliphatic groups $R^1$, $R^2$, and $R^3$ each, for example, are a methyl group, an ethyl group, or a propyl group, and preferably a methyl group or an ethyl group.

The aromatic groups $Ar^1$, $Ar^2$, $Ar^3$, $Ar^4$, $Ar^5$, $Ar^6$, $Ar^7$, and $Ar^8$ in formulae (1), (7), (8), (9), (10), and (11) each, for example, are a phenylene group, a naphthalene group, a phenanthrene group, or a pyrene group, and preferably a phenylene group or a naphthalene group. Z in formulae (1) and (9) is preferably an ether group (—O—).

As the diamine compound of the present invention, A in formula (1) is preferably the aliphatic group $R^1$ or the aromatic group $Ar^1$, more preferably the aromatic group $Ar^1$.

Examples of the diamine compound of the present invention include 2,7-bis(aminomethoxy)fluorene, 2,7-bis(aminoethoxy)fluorene, 2,7-bis(3-aminopropoxy)fluorene, 2,7-bis(2-aminopropoxy)fluorene, 2,7-bis(4-aminobutoxy)fluorene, 2,7-bis(3-aminobutoxy)fluorene, 2,7-bis(2-aminobutoxy)fluorene, 2,7-bis(5-aminopentoxy)fluorene, 2,7-bis(4-aminopentoxy)fluorene, 2,7-bis(3-aminopentoxy)fluorene, 2,7-bis(2-aminopentoxy)fluorene, 2,7-bis(6-aminohexyloxy)fluorene, 2,7-bis(5-aminohexyloxy)fluorene, 2,7-bis(4-aminohexyloxy)fluorene, 2,7-bis(3-aminohexyloxy)fluorene, 2,7-bis(2-aminohexyloxy)fluorene, 2,7-bis(1-amino-1-phenylmethoxy)fluorene, 2,7-bis[1-(4-aminophenyl)methoxy]fluorene, 2,7-bis[1-(3-aminophenyl)methoxy]fluorene, 2,7-bis[1-(2-aminophenyl)methoxy]fluorene, 2,7-bis(2-amino-2-phenylethoxy)fluorene, 2,7-bis(2-amino-2-phenoxyethoxy)fluorene, 2,7-bis(2-amino-2- phenylsulfanylethoxy)fluorene, 2,7-bis(2-amino-2-benzenesulfonylethoxy)fluorene, 2,7-bis(3-amino-2-phenylpropoxy)fluorene, 2,7-bis(3-amino-2-phenoxypropoxy)fluorene, 2,7-bis(3-amino-2-phenylsulfanylpropoxy)fluorene, 2,7-bis(3-amino-2-benzenesulfonylpropoxy)fluorene, 2,7-bis(4-amino-2-phenylbutoxy)fluorene, 2,7-bis(4-amino-2-phenoxybutoxy)fluorene, 2,7-bis(4-amino-2-phenylsulfanylbutoxy)fluorene, 2,7-bis(4-amino-2-benzenesulfonylbutoxy)fluorene, 2,7-bis(4-amino-3-phenylbutoxy)fluorene, 2,7-bis(4-amino-3-phenoxybutoxy)fluorene, 2,7-bis(4-amino-3-phenylsulfanylbutoxy)fluorene, 2,7-bis(4-amino-3-benzenesulfonylbutoxy)fluorene, 2,7-bis(5-amino-3-phenylpentoxy)fluorene, 2,7-bis(5-amino-3-phenoxypentoxy)fluorene, 2,7-bis(5-amino-3-phenylsulfanylpentoxy)fluorene, 2,7-bis(5-amino-3-benzenesulfonylpentoxy)fluorene, 2,7-bis(4-aminophenoxy)fluorene, 2,7-bis(3-aminophenoxy)fluorene, 2,7-bis(2-aminophenoxy)fluorene, 2,7-bis(5-amino-1-naphthoxy)fluorene, 2,7-bis(8-amino-1-naphthoxy)fluorene, 2,7-bis(3-amino-2-naphthoxy)fluorene, 2,7-bis(8-amino-2-naphthoxy)fluorene, 2,7-bis(4-amino-1-naphthoxy)fluorene, 2,7-bis(2-amino-1-naphthoxy)fluorene, 2,7-bis(6-amino-2-naphthoxy)fluorene, 2,7-bis(7-amino-2-naphthoxy)fluorene, 2,7-bis(6-amino-1-pyrenoxy)fluorene, 2,7-bis(8-amino-1-pyrenoxy)fluorene, 2,7-bis(3-amino-1-pyrenoxy)fluorene, 2,7-bis(10-amino-9-phenanthrenoxy)fluorene, 2,7-bis(7-amino-2-fluorenoxy)fluorene, 2,7-bis(4'-amino-4-biphenyloxy)fluorene, 2,7-bis(4'-amino-3,3'-dimethyl-4-biphenyloxy)fluorene, 2,7-bis{4-[1-(4-aminophenyl)-2,2,2-trifluoro-1-trifluoromethylethyl]phenoxy}fluorene, 2,7-bis[4-(4-aminophenoxy)phenoxy]fluorene, 2,7-bis[4-(4-aminophenylsulfanyl)phenoxy]fluorene, 2,7-bis[4-(4-aminobenzenesulfonyl)phenoxy]fluorene, 2,7-bis(8-amino-3-phenanthridineoxy)fluorene, 2,7-bis(3-amino-8-phenanthridineoxy)fluorene, 2,7-bis(8-amino-6-phenyl-3-phenanthridineoxy)fluorene, and 2,7-bis(3-amino-6-phenyl-8-phenanthridineoxy)fluorene.

In the diamine compound of the present invention, a substituent having an amino group is bonded via an ether bond (—O—) to each of the carbon atoms at the 2-position and the 7-position. The ether bond allows excellent rotatability of molecular chains. Thus, a polymer formed with the diamine compound can realize a film having, for example, high bending properties and high flexibility induced by this bond.

The diamine compound of the present invention can be used in the same applications as conventional diamine compounds. Examples of the application include a raw material or a crosslinking agent for thermosetting polymers or polycondensation polymers such as polyamide, polyimide, epoxy resin, and polyurethane.

<Method for Producing a Diamine Compound of the Present Invention>

In the method for producing a diamine compound of the present invention, the 2,7-dihydroxy-9-fluorenone represented by formula (2) and the compound (A) represented by formula (3) are first subjected to condensation to obtain the compound (B) represented by formula (4) (Reaction 1).

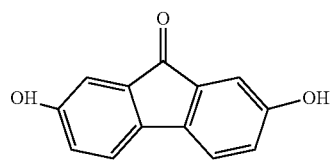

(2)

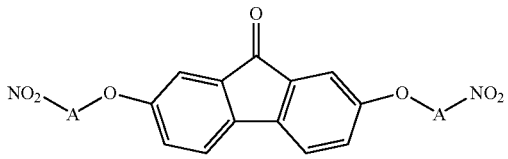

X in formula (3) denotes halogen group (F, Cl, Br, or I, among which F, Cl, or Br is preferred and F or Cl is more preferred). For example, A in formula (3) denotes a divalent hydrocarbon group which may have a substituent and has a carbon number of 1 to 10. As a preferred example, A in formula (3) denotes: a divalent aliphatic group $R^1$ which may have a substituent and has a carbon number of 1 to 10; a divalent aromatic group $Ar^1$ which has 1 to 4 ring structures and may have a substituent; a group, composed of divalent aromatic groups $Ar^2$ and $Ar^3$ each of which has 1 to 4 ring structures and may have a substituent, represented by the formula [—$Ar^2$—$Ar^3$—] (where $Ar^2$ and $Ar^3$ may be the same as or different from each other); a group, composed of divalent aromatic groups $Ar^4$ and $Ar^5$ each of which has 1 to 4 ring structures and may have a substituent, and Z which is an ether group (—O—), a thioether group (—S—) or a sulfone group (—$SO_2$—), represented by the formula [—$Ar^4$—Z—$Ar^5$—] (where $Ar^4$ and $Ar^5$ may be the same as or different from each other); a group, composed of a divalent aromatic group $Ar^6$ which has 1 to 4 ring structures and may have a substituent, and a divalent aliphatic group $R^2$ which may have a substituent and has a carbon number of 1 to 10, represented by the formula [—$Ar^6$—$R^2$—]; or a group, composed of divalent aromatic groups $Ar^7$ and $Ar^8$ each of which has 1 to 4 ring structures and may have a substituent, and a divalent aliphatic group $R^3$ which may have a substituent and has a carbon number of 1 to 10, represented by the formula [—$Ar^7$—$R^3$—$Ar^8$—] (where $Ar^7$ and $Ar^8$ may be the same as or different from each other). The above-mentioned substituent which the aliphatic groups $R^1$, $R^2$, and $R^3$, and the aromatic groups $Ar^1$, $Ar^2$, $Ar^3$, $Ar^4$, $Ar^5$, $Ar^6$, $Ar^7$, and $Ar^8$ may have is at least one selected from a methyl group, an ethyl group, a propyl group, a butyl group, a trifluoromethyl group, a phenyl group, a phenoxy group, a phenylthio group, and a benzenesulfonyl group.

A in formula (3) may be selected corresponding to the substituent having an amino group contained in the target diamine compound. For example, when the target diamine compound is expressed by formula (1), the A in formula (3) may be the same as in formula (1). The A appearing in formulae (4) and (5) is the same as in formula (3), as long as the molecular structure does not change through the intermediate reactions.

As a specific example, A in formula (3) denotes a phenylene group, a naphthalene group, a methyl group, and an ethyl group.

Reaction 1 is a dehydrohalogenation condensation reaction as well as an etherification reaction between the compound (A) and the hydroxy group of 2,7-dihydroxy-9-fluorenone, which proceeds efficiently in the presence of a basic catalyst.

The basic catalyst, for example, is oxides, hydroxides, carbonates, hydrogencarbonates, hydrides, and alkoxides of alkali metals. Specific examples thereof include sodium oxide, lithium oxide, potassium hydroxide, sodium hydroxide, lithium hydroxide, potassium carbonate, sodium carbonate, potassium bicarbonate, sodium bicarbonate, sodium hydride, potassium t-butoxide, sodium methoxide, and sodium ethoxide. Two or more types of catalysts may be used. The use amount of catalyst, for example, is an equivalent mole of 1.0 to 5.0, preferably an equivalent mole of 2.0 to 4.0, with respect to 2,7-dihydroxy-9-fluorenone.

In Reaction 1, the reaction solvent is not specifically limited as long as Reaction 1 proceeds, but is preferably a polar aprotic solvent. Examples of the reaction solvent in Reaction 1 include N-methylformamide, N,N-dimethylformamide, N,N-dimethylacetamide, dimethylsulfoxide, dimethylsulfone, sulfolane, N-methyl-2-pyrrolidinone, N-methylpyrrolidone (NMP), 1,3-dimethyl-2-imidazolidinone, N,N,N',N'-tetramethylurea, hexamethylphosphotriamide, 1,3-dimethyl-3,4,5,6-tetrahydro-2(1H)-pyrimidinone, tetrahydrofuran, acetonitrile, and acetone. The use amount of reaction solvent is not specifically limited, but is generally 1 to 20 times by weight the total amount of reactant. The polar aprotic solvent can be used continuously as a reaction solvent in Reactions 2 and 3 after Reaction 1.

In Reaction 1, quaternary ammonium salts, quaternary phosphates, macrocyclic polyethers such as crown ethers, nitrogen-containing macrocyclic polyethers such as cryptates, nitrogen-containing chain polyethers, phase transfer catalysts such as polyethylene glycols and alkyl ethers thereof, copper powder, copper salts, etc., may be used in combination as a reaction accelerator.

Specific reaction conditions such as the reaction temperature and reaction time can be appropriately adjusted.

In Reaction 1, binding of a substituent to the carbon atom at the 9-position is suppressed due to the use of fluorenone having a ketone group at the 9-position in the fluorene skeleton as a starting material. Thereby, the diamine compound of the present invention can be efficiently produced by subsequently performing the Reactions 2 and 3. It was confirmed by the inventors that a substituent was bonded to the carbon atom at the 9-position in the case of allowing the same reaction as Reaction 1 to proceed using 2,7-dihydroxy-9-fluorene as a starting material instead of 2,7-dihydroxy-9-fluorenone.

Next, the ketone group at the 9-position of the compound (B) obtained after Reaction 1 is reduced to the state where a hydroxy group is bonded to the carbon atom at the 9-position, and thereafter the hydroxy group is acetylated. Thus, the compound (C) represented by formula (5) is obtained (Reaction 2).

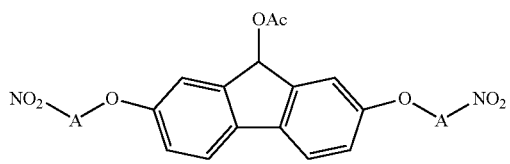

(5)

In order to obtain the diamine compound of the present invention, the ketone group at the 9-position of the compound (B) is required to be reduced to a methylene group. However, the reduction of the ketone group of the compound (B) does not proceed any further than the state where a hydroxy group is bonded to the carbon atom at the 9-position. Therefore, after the reduction has proceeded to the state where the hydroxy group is bonded to the carbon atom at the 9-position, the hydroxy group is once acetylated to the state where an acetoxy group (—OAc) is bonded thereto. It is not until this state (the state of the compound (C)) has been achieved that it becomes possible to reduce the ketone group at the 9-position in the fluorene skeleton to a methylene group.

In Reaction 2, the reduction of the ketone group may be allowed to proceed, for example, by techniques such as hydrogenation, hydride reduction, and metal reduction. Reductants and/or catalysts to be used in the respective techniques are not specifically limited. For hydrogenation and metal reduction, fine powder of a metal such as nickel, copper-chromium oxide, ruthenium, rhodium, and platinum; a catalyst obtained by allowing such fine powder to be adsorbed on an insoluble carrier such as activated carbon, alumina, and diatomite; or a complex of an organic compound and a metal, for example, can be used. For hydride reduction, diborane, sodium borohydride ($NaBH_4$), sodium cyanoborohydride, lithium triethylborohydride, lithium tri(sec-butyl)borohydride, potassium tri(sec-butyl)borohydride, diisobutylaluminum hydride, lithium aluminum hydride, sodium bis(2-methoxyethoxy)aluminum hydride, or tributyltin hydride, for example, can be used.

As a reaction solvent to be used for the reduction of the ketone group, an appropriately selected solvent can be used as long as the reduction proceeds. In the case of using a polar aprotic solvent as a reaction solvent in Reaction 1, it also is possible to use the solvent continuously.

Specific reaction conditions such as the reaction temperature and reaction time can be appropriately adjusted.

The acetylation in Reaction 2 may be allowed to proceed, for example, using acetic anhydride or acetyl chloride.

As a reaction solvent to be used for the acetylation, an appropriately selected solvent can be used as long as the acetylation proceeds. In the case of using a polar aprotic solvent as a reaction solvent in Reaction 1, it also is possible to use the solvent continuously.

Specific reaction conditions such as the reaction temperature and reaction time can be appropriately adjusted.

Next, the diamine compound of the present invention represented by formula (1) is obtained by reducing, to a methylene group, the carbon atom (carbon atom to which the acetoxy group is bonded) at the 9-position in the fluorene skeleton of the compound (C) obtained after Reaction 2 and reducing, to amino groups, the nitro groups included in the compound (A)-derived substituents that are bonded to the carbon atoms at the 2-position and the 7-position (Reaction 3).

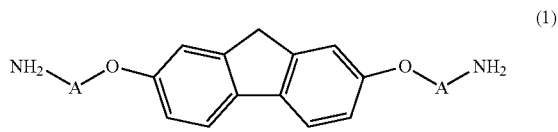

(1)

In Reaction 3, the reductions may be allowed to proceed, for example, by techniques such as hydrogenation, hydride reduction, and metal reduction. Reductants and/or catalysts to be used in the respective techniques may be the same as those used for the reduction of the ketone group in Reaction 2. Specific reaction conditions such as the reaction temperature and reaction time can be appropriately adjusted.

As a reaction solvent to be used for Reaction 3, an appropriately selected solvent can be used as long as Reaction 3 proceeds. In the case of using a polar aprotic solvent as a reaction solvent in Reaction 1, it also is possible to use the solvent continuously.

In Reaction 3, the reduction of the carbon atom at the 9-position and the reduction of the nitro groups may be performed simultaneously or separately.

In the production method of the present invention, optional reactions or optional steps other than Reactions 1, 2, and 3 may be performed additionally, as needed.

EXAMPLE

Hereinafter, the present invention is described further in detail with reference to the example. The present invention is not limited to the following example.

<Reaction 1>

100.0 g (471.3 mmol) of 2,7-dihydroxy-9-fluorenone, 146.3 g (1036.8 mmol) of 4-fluoronitrobenzene as the compound (A), 260.5 g (1885.0 mmol) of potassium carbonate as a catalyst, and 1000 mL of N-methylpyrrolidone (NMP) as a reaction solvent were put into a four-necked separable flask with an internal volume of 2 L. Under stirring, the mixture in the flask was subjected to the reaction represented by formula (12) below in a nitrogen atmosphere at 90° C. for 3 hours. After the completion of the reaction, the contents of the flask were cooled to room temperature. Thereafter, they were poured into 10 L of ice water and precipitated crystal was collected by filtration. The collected crystal was washed sequentially with water and ethanol, followed by drying under reduced pressure. Thus, 197.4 g (yield rate: 92.2%) of the compound (B) shown on the right-hand side of formula (12) was obtained as an ocherous crystal. The compound (B) shown on the right-hand side of formula (12) is 2,7-bis(4-nitrophenoxy)-9-fluorenone.

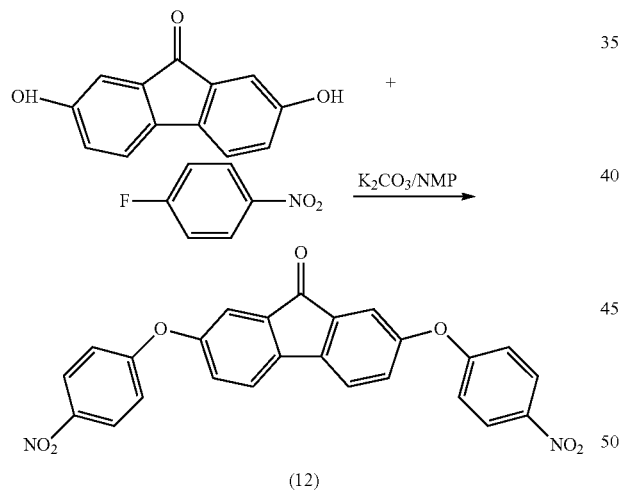

(12)

<Reaction 2>

150.0 g (330.1 mmol) of the compound (B) obtained by Reaction 1, 61.2 g (1617.6 mmol) of sodium borohydride and 123.3 g (924.3 mmol) of aluminum chloride (III) as a reductant, and 2.3 L of tetrahydrofuran (THF) as a reaction solvent were put into a four-necked separable flask with an internal volume of 5 L. The mixture in the flask was allowed to circulate in a nitrogen atmosphere for one night so as to be subjected to the reaction represented by formula (13) below. Then, 1 L of water was added dropwise to the flask under cooling in an ice bath to cause quenching. Next, the reaction product was extracted with ethyl acetate and the extract was dried with sodium sulfate, which thereafter was concentrated under reduced pressure to undergo crystallization with heptane. Thus, 154.1 g (yield rate: 102.3%) of the compound (2,7-bis(4-nitrophenoxy)-9-hydroxyfluorene) shown on the right-hand side of formula (13) was obtained as a yellow crystal.

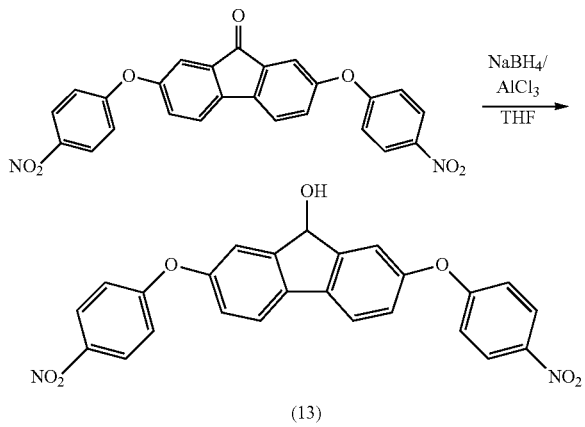

(13)

Next, 150.0 g (328.7 mmol) of the resultant compound, 2 L of dichloromethane, 39.9 g (394.4 mmol) of triethylamine, and 4.0 g (32.9 mmol) of N,N-dimethyl-4-aminopyridine (DMAP) were put into a four-necked separable flask with an internal volume of 3 L. The whole was cooled with ice, while a nitrogen atmosphere was maintained inside the flask. Then, 31.0 g (394.4 mmol) of acetyl chloride was added dropwise thereto, which was stirred for 3 hours. Thereafter, the temperature of the mixture in the flask was returned to room temperature and stirred for one night continuously so as to be subjected to the reaction represented by formula (14) below. After the contents of the flask was poured into 3 L of ice water, the reaction product was extracted with dichloromethane and the extract was dried with sodium sulfate, which thereafter was concentrated under reduced pressure. The residue thus obtained was purified by column chromatography (using 1000 g of silica gel and dichloromethane as a developing solvent). The thus obtained crystal was crystallized with THF/heptane. Thus, 159.7 g (yield rate: 97.5%) of the compound (C) shown on the right-hand side of formula (14) was obtained as a pale orange crystal. The compound (C) shown on the right-hand side of formula (14) is 2,7-bis(4-nitrophenoxy)-9-acetoxyfluorene.

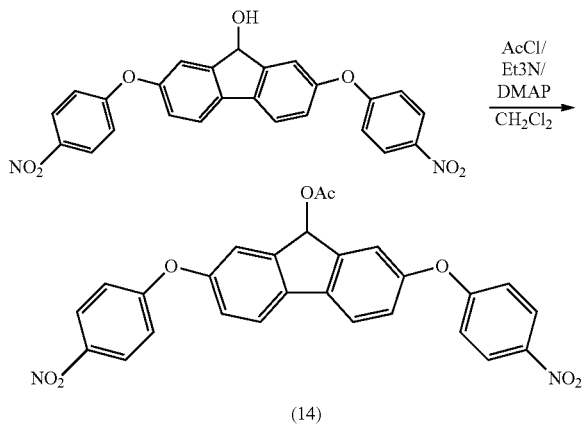

(14)

<Reaction 3>

159.0 g (319.0 mmol) of the compound (C) obtained by Reaction 2, 15.9 g of a 10-wt % palladium-activated carbon ethylenediamine complex as a reductant, and 3 L of THF as a reaction solvent were put into a four-necked separable flask with an internal volume of 5 L. The contents of the flask were stirred continuously at room temperature for 2 days, while a hydrogen atmosphere was maintained inside the flask, so as to be subjected to the reaction represented by formula (15) below. After the completion of the reaction, the catalyst was removed from the contents of the flask by Celite filtration. Thereafter, the filtrate was concentrated under reduced pressure, which was crystallized with heptane. The crystallized crystal was further dissolved in a small amount of THF, which was crystallized with THF/ethanol. Thus, 101.1 g (yield rate: 83.3%) of 2,7-bis(4-aminophenoxy)fluorene shown on the right-hand side of formula (15) was obtained.

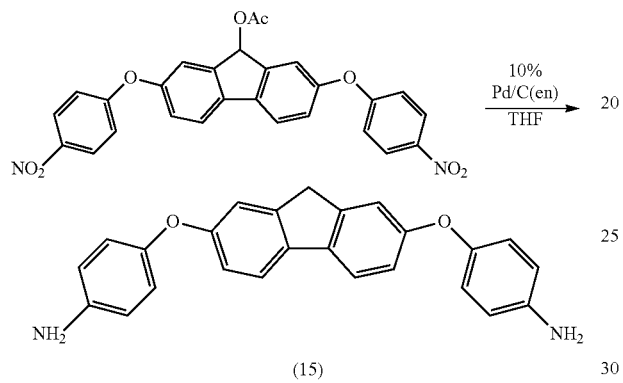

The resultant 2,7-bis(4-aminophenoxy)fluorene was identified by the proton nuclear magnetic resonance spectroscopy (¹H-NMR, AVANCE II 300, manufactured by Bruker BioSpin Corporation, with a frequency of 300 MHz, using dimethylsulfoxide-d6 as a solvent for measurement). FIG. 1 shows the results of the NMR measurement. As shown in FIG. 1, peaks at 3.785 ppm (2H), 4.977 ppm (4H), 6.577-6.607 ppm (4H), 6.770-6.799 ppm (4H), 6.850-6.885 ppm (2H), 6.992-6.999 ppm (2H), and 7.680-7.708 ppm (2H) were observed in the chemical shift σ. Thus, it was confirmed to be 2,7-bis(4-aminophenoxy)fluorene.

INDUSTRIAL APPLICABILITY

The diamine compound of the present invention can be used in the same applications as conventional diamine compounds. The applications are, for example, a raw material or a crosslinking agent for thermosetting polymers or polycondensation polymers such as polyamide, polyimide, epoxy resin, and polyurethane.

The invention claimed is:
1. A method for producing the diamine compound represented by formula (1) below,

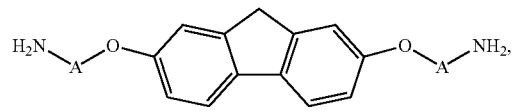

the method comprising steps of:
obtaining a compound (B) represented by formula (4) below by a condensation reaction between 2,7-dihydroxy-9-fluorenone represented by formula (2) and a compound (A) represented by formula (3), obtaining a compound (C) represented by formula (5) below by reducing a ketone group at the 9-position in a fluorene skeleton of the compound (B) to a state where a hydroxy group is bonded to a carbon atom at the 9-position, and thereafter acetylating the hydroxy group, obtaining a diamine compound represented by the formula (1) by reducing the carbon atom at the 9-position, to which the acetoxy group is bonded, in the fluorene skeleton of the compound (C), and reducing nitro groups included in the compound (A)-derived substituents that are bonded to carbon atoms at the 2-position and the 7-position in the skeleton, wherein X in formula (3) denotes a halogen group, and
A in formulae (1) and from (3) to (5) denotes:
a divalent aliphatic group R¹, which may have a substituent and has a carbon number from 1 to 10;
a divalent aromatic group Ar¹, which has from 1 to 4 ring structures and may have a substituent;
a group composed of divalent aromatic groups Ar² and Ar³, each of which has from 1 to 4 ring structures and may have a substituent, the group being represented by a formula [—Ar²—Ar³—] (where Ar² and Ar³ may be same as or different from each other);

a group composed of divalent aromatic groups $Ar^4$ and $Ar^5$, each of which has from 1 to 4 ring structures and may have a substituent, and Z, which is an ether group (—O—), a thioether group (—S—), or a sulfone group (—$SO_2$—), the group being represented by a formula [—$Ar^4$—Z—$Ar^5$-] (where $Ar^4$ and $Ar^5$ may be same as or different from each other);

a group composed of a divalent aromatic group $Ar^6$, which has from 1 to 4 ring structures and may have a substituent, and a divalent aliphatic group $R^2$, which may have a substituent and has a carbon number from 1 to 10, the group being represented by a formula [—$Ar^6$—$R^2$—]; or a group composed of divalent aromatic groups $Ar^7$ and $Ar^8$, each of which has from 1 to 4 ring structures and may have a substituent, and a divalent aliphatic group $R^3$, which may have a substituent and has a carbon number from 1 to 10, the group being represented by a formula [—$Ar^7$—$R^3$—$Ar^8$—] (where $Ar^7$ and $Ar^8$ may be same as or different from each other), wherein the substituent is at least one group selected from a methyl group, an ethyl group, a propyl group, a butyl group, a trifluoromethyl group, a phenyl group, a phenoxy group, a phenylthio group, and a benzenesulfonyl group.

2. The method according to claim 1, wherein in the step of obtaining the diamine compound represented by the formula (1), the actoxy group and the nitro groups are reduced simultaneously.

3. The method according to claim 1, wherein in the step of obtaining the diamine compound represented by the formula (1), the actoxy group and the nitro groups are reduced separately.

* * * * *